United States Patent
Westby et al.

(10) Patent No.: US 10,977,883 B2
(45) Date of Patent: Apr. 13, 2021

(54) SYSTEMS AND METHODS OF USING IMPLANTED OR WEARABLE MICRO ELECTRONIC DEVICES AND FOR USING A MOBILE DEVICE TO COMMUNICATE WITH AND MANAGE SUCH MICRO ELECTRONIC DEVICES

(71) Applicants: Todd Westby, Woodbury, MN (US); Eric Bloms, River Falls, WI (US); Sam Bengston, River Falls, WI (US); Patrick McMullan, Gilbert, AZ (US)

(72) Inventors: Todd Westby, Woodbury, MN (US); Eric Bloms, River Falls, WI (US); Sam Bengston, River Falls, WI (US); Patrick McMullan, Gilbert, AZ (US)

(73) Assignee: T.W. Vending, Inc., River Falls, WI (US)

( * ) Notice: Subject to any disclaimer, the term of this patent is extended or adjusted under 35 U.S.C. 154(b) by 0 days.

(21) Appl. No.: 16/368,035

(22) Filed: Mar. 28, 2019

(65) Prior Publication Data
US 2020/0402331 A1 Dec. 24, 2020

Related U.S. Application Data

(62) Division of application No. 16/052,170, filed on Aug. 1, 2018, now Pat. No. 10,311,662.

(51) Int. Cl.
*G07C 9/00* (2020.01)
*A61B 5/07* (2006.01)
(Continued)

(52) U.S. Cl.
CPC .......... *G07C 9/00309* (2013.01); *A61B 5/076* (2013.01); *G06Q 20/18* (2013.01);
(Continued)

(58) Field of Classification Search
CPC ...... A61B 5/076; A61B 5/1118; H04B 13/005
See application file for complete search history.

(56) References Cited

U.S. PATENT DOCUMENTS

2005/0133701 A1* 6/2005 Anderson, II ....... A01K 15/021
250/221
2005/0274463 A1* 12/2005 Becker ..................... E06B 7/32
160/98

(Continued)

*Primary Examiner* — Fabricio R Murillo Garcia
(74) *Attorney, Agent, or Firm* — Skinner and Associates; Joel D. Skinner, Jr.

(57) ABSTRACT

A system, apparatus and method utilize a micro electronic device implanted in a person or group of persons, or wearable thereby, to manage a variety of activities, including interrogating an RF microdevice for information. The microdevice has a housing, an antenna, a microprocessor, a tuning capacitor, and a transducer such as a location transponder, a thermometer, a heart rate transducer, a blood pressure transducer, and an information storage element. The method includes the steps of providing the microdevice and attaching it to a person. The person brings the microdevice near a login system having an RF reader and a login processor. The reader communicates with the microdevice via RF signals, and signals the login processor to corroborate an identification code from the microdevice. If the login processor corroborates the identification code, it signals the microdevice to permit access to information from the transducer. If the login processor does not corroborate the identification code, access to the information is not permitted.

2 Claims, 17 Drawing Sheets

(51) Int. Cl.
*H04B 13/00* (2006.01)
*G06Q 20/18* (2012.01)
*H04W 4/90* (2018.01)
*H04W 12/06* (2021.01)
*H04L 29/06* (2006.01)
*G06Q 20/32* (2012.01)
*G07F 7/08* (2006.01)

(52) U.S. Cl.
CPC ....... *G06Q 20/3278* (2013.01); *H04B 13/005* (2013.01); *H04L 63/0853* (2013.01); *H04W 4/90* (2018.02); *H04W 12/06* (2013.01); *G07C 2009/00507* (2013.01); *G07C 2009/00603* (2013.01); *G07C 2009/00769* (2013.01); *G07C 2009/00809* (2013.01); *G07F 7/08* (2013.01); *H04L 29/06802* (2013.01)

(56) References Cited

U.S. PATENT DOCUMENTS

| 2013/0122866 | A1* | 5/2013 | Huang | G06F 21/31 |
| | | | | 455/411 |
| 2015/0304322 | A1* | 10/2015 | Zaidi | H04W 12/06 |
| | | | | 382/115 |

* cited by examiner

SYSTEMS AND METHODS OF USING IMPLANTED OR WEARABLE MICRO ELECTRONIC DEVICES AND FOR USING A MOBILE DEVICE TO COMMUNICATE WITH AND MANAGE SUCH MICRO ELECTRONIC DEVICES

CROSS-REFERENCE TO RELATED APPLICATIONS, IF ANY

This application is a divisional application of co-pending U.S. application Ser. No. 16/052,170, filed Aug. 1, 2018, which claims the benefit under 35 U.S.C. § 119(e) of U.S. Provisional Patent Application Ser. No. 62/677,257, filed May 29, 2018, U.S. Provisional Patent Application Ser. No. 62/551,455, filed Aug. 29, 2017, and U.S. Provisional Patent Application Ser. No. 62/539,698, filed Aug. 1, 2017, which are hereby incorporated by reference.

This application is also a continuation in part of U.S. patent application Ser. No. 14/874,855, filed Oct. 5, 2015, status pending, which is a continuation of U.S. patent application Ser. No. 14/332,008, filed Jul. 15, 2014, status patented U.S. Pat. No. 9,171,300, which is a continuation in part of U.S. patent application Ser. No. 14/207,392, filed Mar. 12, 2014.

37 C.F.R. § 1.71(e) AUTHORIZATION

A portion of the disclosure of this patent document contains material which is subject to copyright protection. The copyright owner has no objection to the facsimile reproduction by anyone of the patent document or the patent disclosure, as it appears in the US Patent and Trademark Office patent file or records, but otherwise reserves all copyright rights whatsoever.

STATEMENT REGARDING FEDERALLY SPONSORED RESEARCH OR DEVELOPMENT

Not applicable.

REFERENCE TO A MICROFICHE APPENDIX, IF ANY

Not applicable.

BACKGROUND OF THE INVENTION

1. Field of the Invention

The present invention relates, generally, to micro electronic devices (chip devices) systems, apparatus and methods. Particularly, the invention relates to micro electronic devices implanted in or worn by humans, and for systems and methods of using such implanted devices for a variety of useful functions. Most particularly, the invention relates to systems and methods of using implanted or worn (for example via bracelets, anklets, and the like) devices in groups of humans such as members of an organization, employees of a company, residents of a facility, inmates, or the like, to open doors and access other building facility resources such as telecommunications resources, micro markets, and the like. The invention is useful for other purposes such as patient management of their own individual medical and other personal records, hospital and health clinic or other third party access to private medical records of persons who may be unable to provide such information, computer and network resource login and access (including login to particular accounts and apps thereon), and vehicle door unlock and/or startup.

The invention also relates to:

a. a system and method of using and managing implanted or wearable micro electronic devices via an associated mobile device such as a smart phone, tablet or the like;

b. micro electronic devices embedded in, incorporated into, or otherwise attached to articles, devices, structures or things to track, manage or monitor such articles, devices, structures or things for geo-location or other tracking, monitoring or management services;

c. micro electronic devices implanted in, worn, or carried by humans for geo-location services for agencies responsible for monitoring such person's whereabouts with respect to branches and as stich judicial and law enforcement agencies; and d. micro electronic devices implanted in, worn, or carried by humans for using biometric sensors or transducers to authenticate and transmit vital signs and other health information to clinic or other facility personnel.

The types of mobile devices that the micro electronic devices are communicatively connected to (See (a) above), include smart phones, tablet devices, laptop PC, pod devices, and the like. The micro electronic devices utilize features and devices of the mobile device such as user interface services, programming services, data processing and storage services, telecommunication services, location services, sensor/transducer services, camera services, clock services, temperature and weather services, and the like.

2. Background Information

Existing technology in this field is believed to have significant limitations and shortcomings. For this and other reasons, a need exists for the present invention.

Chips implanted in or worn by humans have been proposed to be used for purposes such as opening building doors in the past. However, insofar as applicant is aware, such proposals and uses have been limited and largely experimental. No sustained, commercially viable facility access uses are known. Implanted chips have also been proposed or used on a limited basis for accessing personal information (such as medical records). Again, applicant is aware of no commercially viable endeavors. And the existing proposals and devices are believed to base significant limitations and shortcomings. One limitation is that, due to the small size and power capacity of such devices, they have little or no capability to be interfaced or controlled by the user, to store or process information, to telecommunicate with other devices or systems, to locate relative to the environment, to act as a sensor for various parameters and biometrics, to take pictures or video, to clock or time events, to sense or determine environmental factors such as temperature, and a variety of other functions. Chips implanted in other animals such as pets and livestock are also known for various purposes. However, none are believed to be similar to Applicants'.

All US patents and patent applications, and all other published documents mentioned anywhere in this application are incorporated by reference in their entirety.

BRIEF SUMMARY OF THE INVENTION

The invention provides an implantable or wearable micro electronic device, implanted in or worn by a human, and systems, apparatus, and methods which are practical, reliable, secure and safe, and which are believed to fulfill the need and to constitute an improvement over the background technology.

The systems and methods of the invention utilize implanted or worn devices, particularly microchips (most particularly RFID microchips) in groups of humans such as members of an organization, employees of a company, residents of a facility or the like, to open doors and access other building/facility resources such as micro markets, commissaries, telecommunications resources, and the like.

The invention is also useful for other purposes such as patient management of their own individual medical and other personal records, hospital and health clinic access to private medical records of persons who may be unable to provide such information, computer and network resource login and access (including login to particular accounts and apps thereon), and vehicle startup.

One aspect of the invention is to provide a means of communicatively connecting the implanted devices to a mobile device, such as a smart phone, whereby the implanted devices utilize features of the mobile device such as user interface services, data processing and storage services, telecommunication services, location services, sensor/transducer services, camera services, clock services, temperature and weather services, and other such services.

In another aspect, the invention provides a method of accessing an electronic device or system (such as an electronic lock, an electronic checkout kiosk at a store, a PC, computer or computer network, a vehicle lock or ignition, or a medical records database), comprising the steps of:
A. providing an RF microdevice having an electronic identification code;
B. attaching the RF microdevice to a user;
C. providing an RF login system, the RF login system including:
  i. at least one RF reader disposed at a predetermined location on or near the device or system, and
  ii. at least one login processor communicatively connected to the at least one RF reader and to a central processor of the device or system, the login processor having means to corroborate the identification code on the RF microdevice:
D. the user brings the RF microdevice near the RF reader, whereby:
  i. the RF reader communicates with the RF microdevice via RF signals, and
  ii. the RF reader signals the login processor to corroborate the identification code, and
    (1) if the login processor corroborates the identification code, the login processor signals the device or system central processor permit electronic access, or
    (2) if the login processor docs not corroborate the identification code, login processor signals the device or system central processor to not permit login.

In a further aspect, the invention provides a system for accessing an electronic device or system (such as an electronic lock, an electronic checkout kiosk at a store, a PC, computer or computer network, a vehicle lock or ignition, or a medical records database), comprising the steps of:
A. an RF microdevice having an electronic identification code adapted to be attached, fixedly or removably, to a user;
B. an RF login system, including:
  i. at least one RF reader disposed at a predetermined location on or near the device or system, and
  ii. at least one login processor communicatively connected to the at least one RF reader and to a central processor of the device or system, the login processor having means to corroborate the identification code on the RF microdevice; and
C. whereby, the user brings the RF microdevice near the RF reader, further whereby:
  i. the RF reader communicates with the RF microdevice via RF signals, and
  ii. the RF reader Signals the login processor to corroborate the identification code, and
    (1) if the login processor corroborates the identification code, the login processor signals the device or system central processor to permit electronic access, or
    (2) if the login processor does not corroborate the identification code, login processor signals the device or system central processor to not permit login.

The aspects, features, advantages, benefits and objects of the invention will become clear to those skilled in the art by reference to the following description, claims and drawings.

BRIEF DESCRIPTION OF THE SEVERAL VIEWS OF THE DRAWING

FIG. 9 illustrates an embodiment of the system and method to enable persons or groups of persons to login and access computer and network resources and devices such as PCs, workstations, laptops, mobile devices and the like.

FIG. 11 illustrates an embodiment of the system and method to enable persons or groups of persons to access and start a vehicle, such as an automobile, truck, bus, and the like.

FIG. 21 shows an embodiment of an alternative system of the invention which includes an implantable or wearable micro device which is communicatively connected to a mobile device such as a smart phone, tablet device, pod device, or the like.

DETAILED DESCRIPTION

A system, apparatus and method utilize a micro electronic device implanted in a person or group of persons, or wearable thereby, to manage a variety of activities. The devices and methods utilize implanted or wearable devices, particularly microchips (most particularly RFID microchips). The micro electronic devices may be implanted in humans or wearable or carried by humans via bracelets and the like, or for, and for systems and methods of using such implanted devices for a variety of useful functions, and for using and managing the micro electronic devices via a mobile device. The microelectronic devices may be used for geo-location services for agencies responsible for monitoring such person's whereabouts with respect to branches and agencies such judicial and law enforcement agencies. The microelectronic devices may be used for biometric sensing to authenticate and transmit vital signs and other health information to clinic or other facility personnel. In an alternative to human use, the micro electronic devices may be embedded in, incorporated into, or otherwise attached to inanimate articles, devices, structures or things to track, manage or monitor such articles, devices, structures or things for geo-location or other tracking, monitoring or management services. Lastly, the micro electronic device may transmit information to and/or from a mobile device whereby the micro electronic devices utilize features of the mobile device such as user interface services, programming services, data processing and storage services, telecommunication services, location services, sensor/transducer services, camera services, clock services, and/or temperature, weather and other services. This also enables tracking, monitoring, inventorying, and management of people and things for medical, legal, business, governmental and various other purposes.

Figure 1:
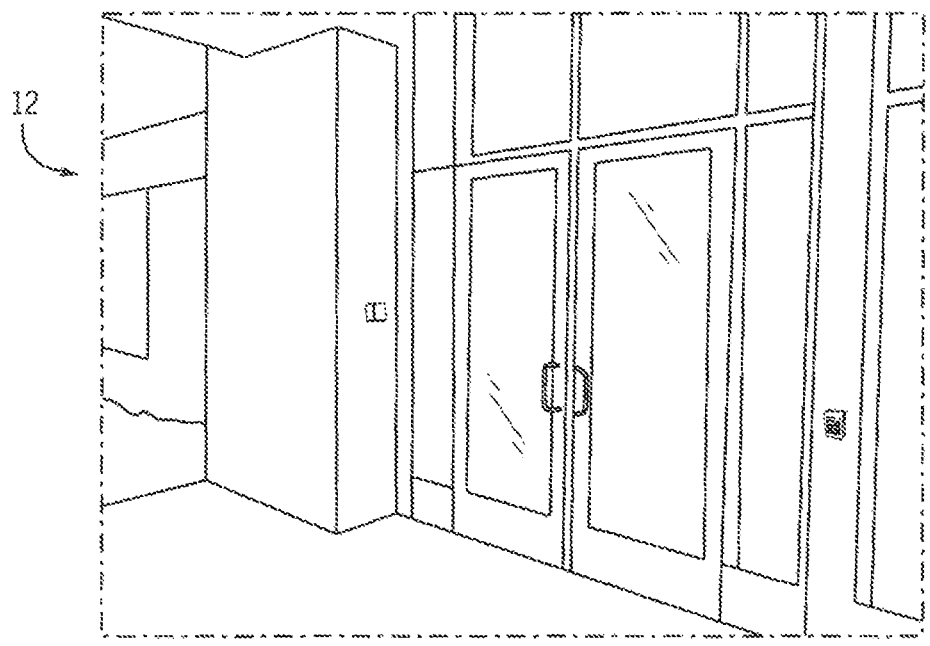
FIG. 1 shows an exemplary environment in which an embodiment of the system of the invention is deployed, a main, outside access door of a private business premises.

FIG. 1 shows an exemplary environment in which an embodiment of the system of the invention is deployed, a main, outside access door 10 of a private business premises 12.

Figure 2:
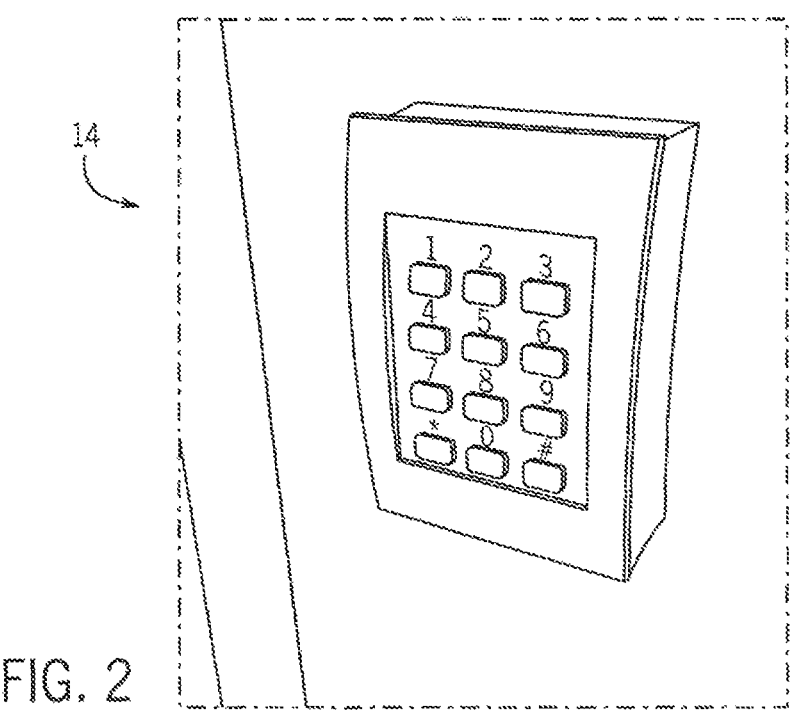
FIG. 2 shows an embodiment of a chip-type micro electronic device reader, which is positioned proximate a door or other ingress/egress means.

FIG. 2 shows an embodiment of a hip type micro electronic desire reader 14, which is positioned proximate a door 10 or other ingress/egress means.

Figure 3:
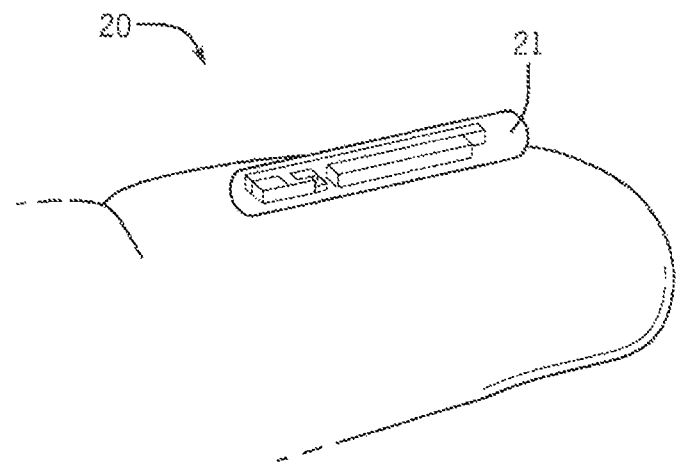
FIG. 3 shows an embodiment of an implantable, chip-type, microelectronic transponder.
Figure 13:
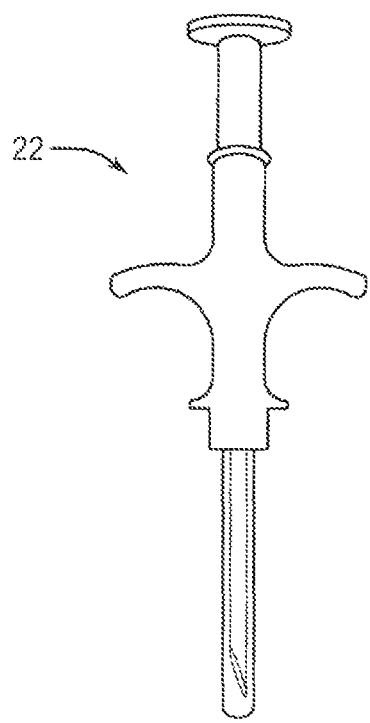
FIG. 13 shows an exemplary implanter assembly for implanting a chip in a user, the chip being contained within the assembly.

FIG. 3 shows art embodiment of an implantable, chip-type, microelectronic transponder 20. In a preferred embodiment, the chip 20 is a passive, RID device. The chip 20 has a very small, predetermined size and geometry that permits implantation below the skin of a human user. In this embodiment, the chip 20 has a housing 21, an antenna 22 disposed inside the housing 21, a microprocessor 23 disposed inside the housing 21 and communicatively connected to the antenna 22, and a tuning capacitor 24 disposed inside the housing 21 and communicatively connected to the processor 23, and wherein the electronic identification code is stored in or by the processor 23. The chip 20 is a passive, dormant device in that it doesn't have an on board power supply. The chip 2—permits access to itself by way of an ancillary RF device, such as a reader, that is connected to power, either via wire or battery. FIG. 13 shows an embodiment of an implanter 22 useable with the chip 20 and systems of the invention. A preferred implantation site is in the hand of the user/member.

Figure 4:
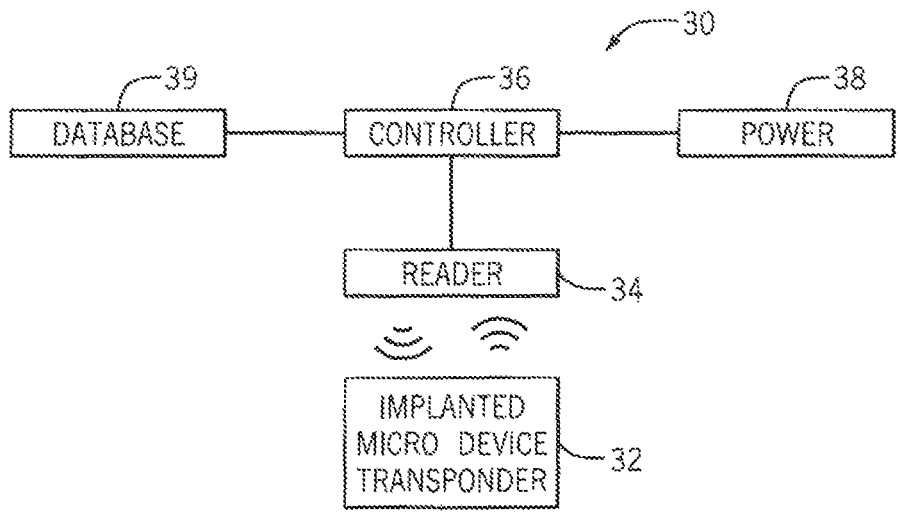
FIG. 4 is a diagram showing an embodiment of a basic system and method of the invention of using an implanted micro electronic device in a human.

FIG. 4 is a diagram showing an embodiment of a basic system and method of using an implanted micro electronic device in a human. The system 30 includes an implantable micro device (IMD) transponder 32 (IMDT) implanted in a user. The system further includes a reader 34 adapted to send signals, for example RF signals, to the chip 32, and to receive information from the chip 32. The reader is communicatively connected to a controller 36. The controller 36 is connected to a power supply 38. The controller 36 is also communicatively connected to a database 39, either internally or externally located. The controller 36 may be further connected to a variety of other devices or elements, such as a door lock or other mechanical device, a display, an input device(s), various communication devices or links, and the like.

Figure 5:
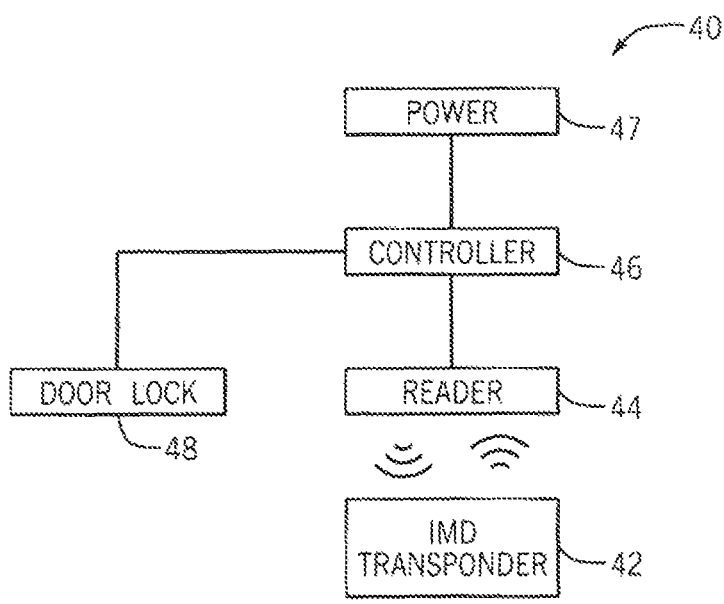
FIG. 5 illustrates an embodiment of a system and method to enable persons or groups of persons to open outside and inside doors and other closures in buildings, facilities, and other premises.

FIG. 5 illustrates an embodiment of a system and method to enable persons or groups of persons to open outside and inside doors and other closures in buildings, facilities, and other premises. The system 40 comprises a an IMDT 42, a reader 44, a controller 46, a power supply 47, and a door lock 48 (preferably disposed proximate the reader 44.

Figure 6:
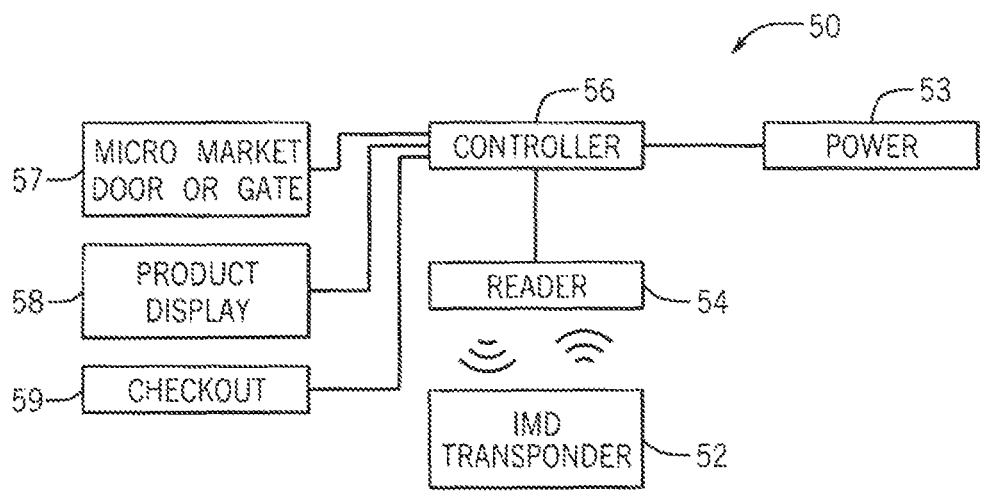
FIG. 6 illustrates an embodiment of the system and method to enable persons or groups of persons to open access, use and check out of various resources and services within a building, including specifically micro markets and commissaries.
Figure 14A:
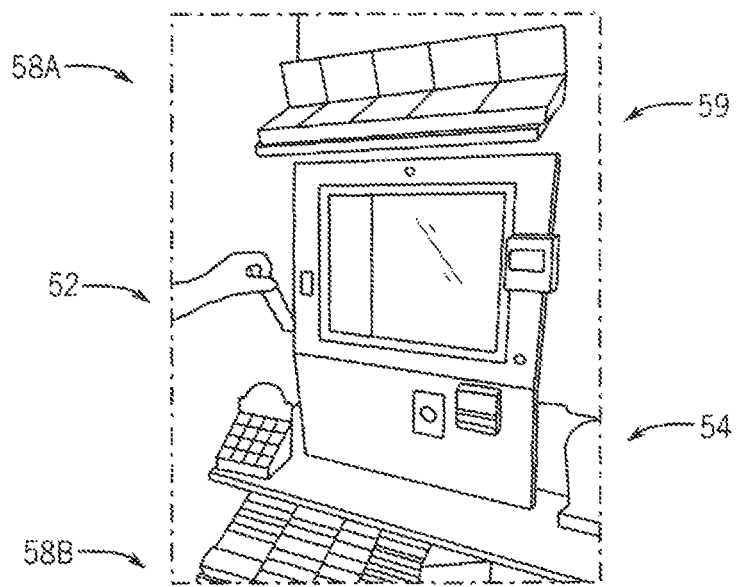
FIGS. 14A-C show an embodiment of a method of using the system of the invention in a Micro Market to purchase products.
Figure 14B:
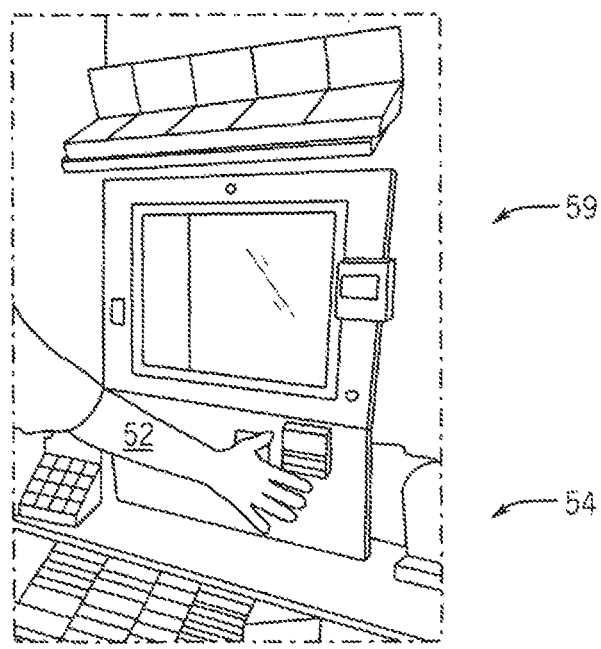
Figure 14C:
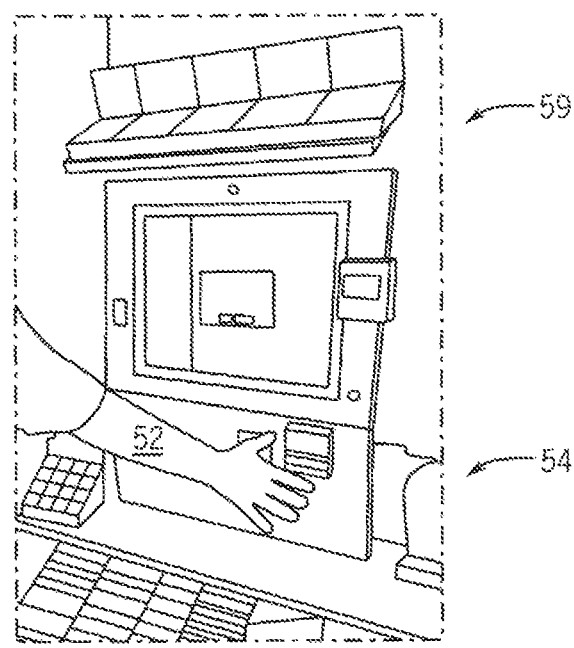

FIG. 6 illustrates using a system and method to enable persons or groups of persons, such as employees, club members, building residents (such as hotel/motel guests, apartment tenants, or condo/townhome owners) and the like, to open access, use and check out of various resources and services within a building, including specifically micro markets. The system 50 comprises an IMDT 52, a power supply 53, a reader 54, a controller 56, and various micro market elements such as an access door or gate 57, a product display door (such as a freezer or cooler door) 58 and a checkout station 59. FIGS. 14A to 14C show an embodiment of the system and a method of purchasing an item from a 32 Square™ Micro Market Kiosk checkout station 59 including an RF reader 54, comprising the steps of scanning a product, reading a user's implanted chip 20 (implanted in the user's hand 52) with the reader 54, and verifying that the transaction is correct. An exemplary Micro Market Controller 56 and associated components, which is useable with this system 50 is disclosed in U.S. Pat. No. 9,171,300, issued Oct. 27, 2015 entitled Retail Convenience Market Technology With Enhanced Vendor Administration and User Mobile App Functionality, which is owned by applicants' assignee. U.S. Pat. No. 9,171,300 is hereby incorporated by reference.

The system is also useable by residents of secure facilities such as inmates of a secure facility such as a detention center, jail or prison, to purchase or check out items from a commissary located within the facility.

Figure 7:
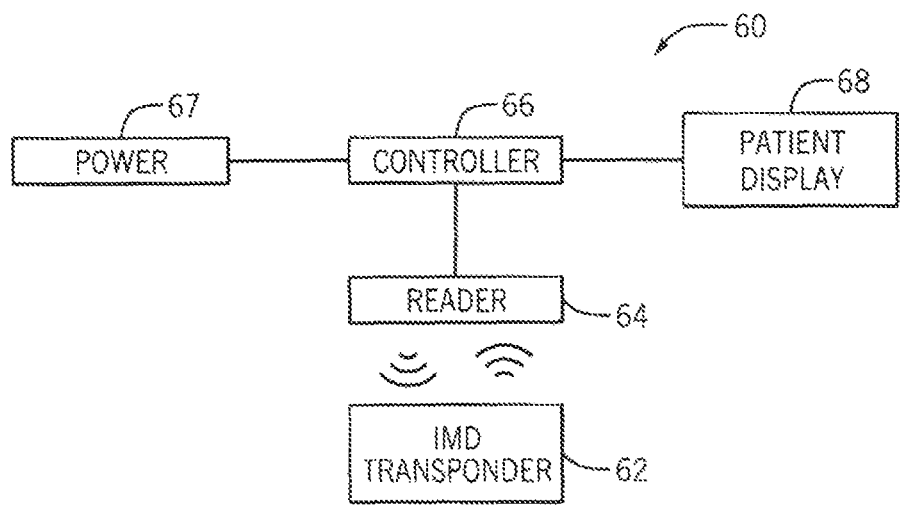
FIG. 7 illustrates an embodiment of the system and method to securely store a person's confidential information, such as medical information, and for that person (the user/owner) to transport, access, manage, and use such private information.

FIG. 7 illustrates using a system and method to securely store a person's confidential information, such as medical information, and for that person (the user/owner) to transport, access, manage, and use such private information. The system 60 comprises an IMDT 62, a reader 64, a controller 66, a power supply 67, and a display device 68 that can be viewed by the user.

Figure 8:
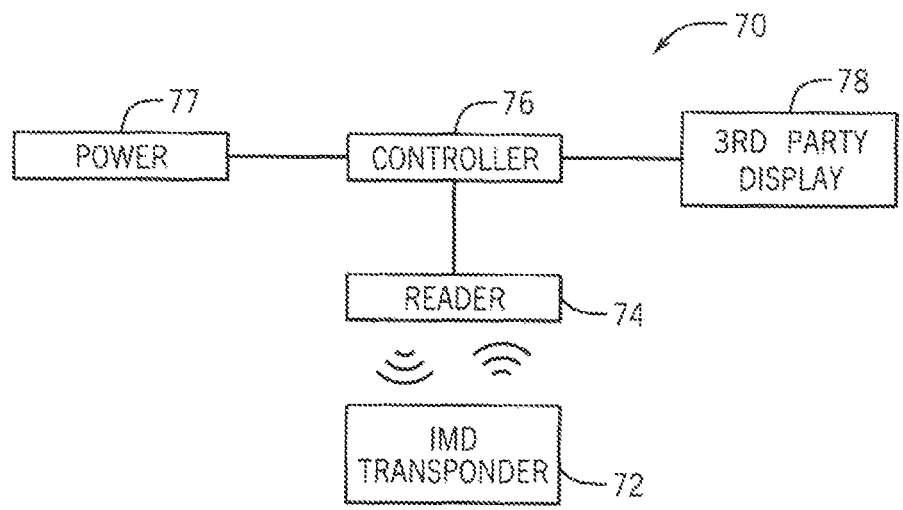
FIG. 8 illustrates an embodiment of the system and method to securely store a persons confidential information, such as medical information, and for a trusted third party, such as a doctor (clinic or hospital), lawyer, or other trusted entity, to access, manage, and use such information to assist the user/owner.

FIG. 8 illustrates using a system and method to securely store a person's confidential information, such as medical information, and for a trusted third party, such as a doctor (clinic or hospital), lawyer, or other trusted entity, to access, manage, and use such information to assist the user/owner. The system 70 comprises an IMDT 72, a reader 74, a controller 76, a power supply 77, and a display device 78 that can be viewed by a trusted third party such as a doctor or other healthcare provider at a clinic, hospital or the like.

Figure 9:
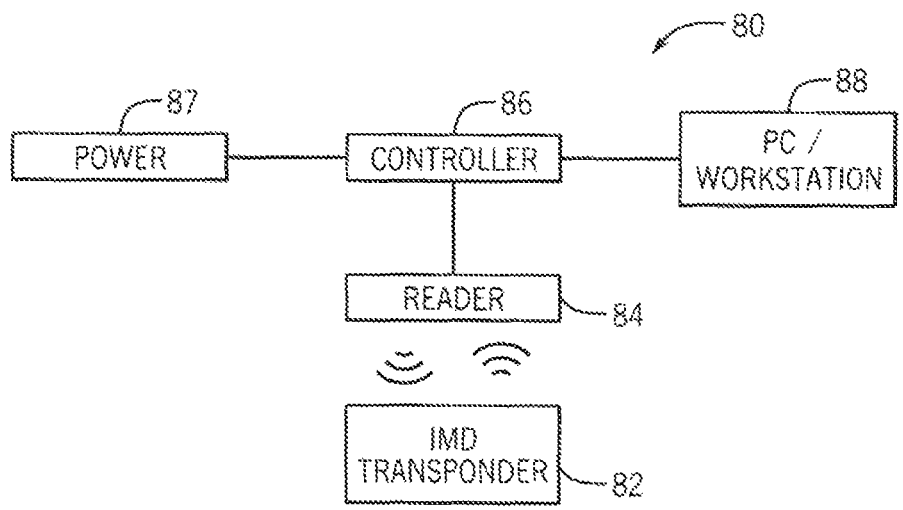
Figure 15A:
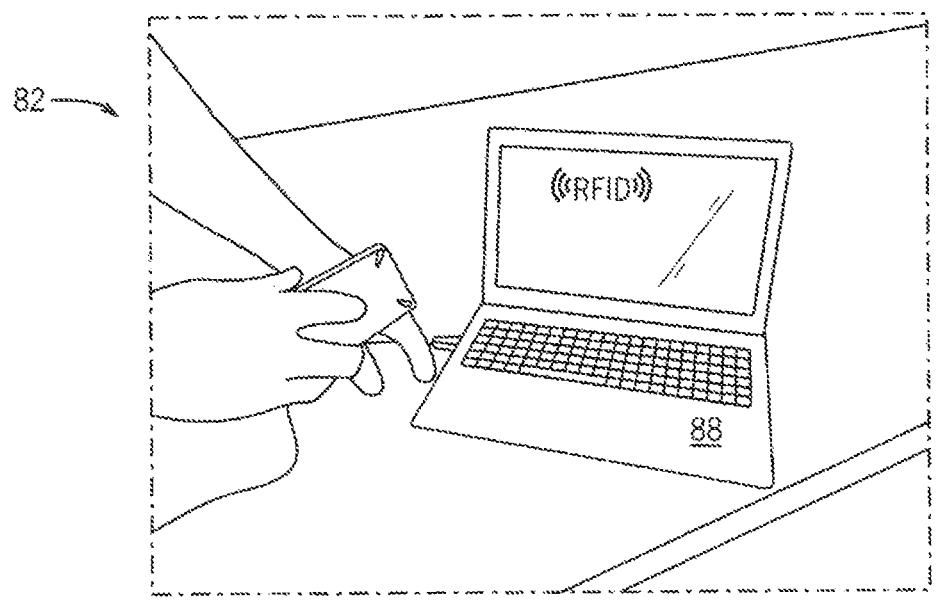
FIGS. 15A and B show an embodiment of a method of using the system of the invention to login to a Personal Computer (PC).
Figure 15B:
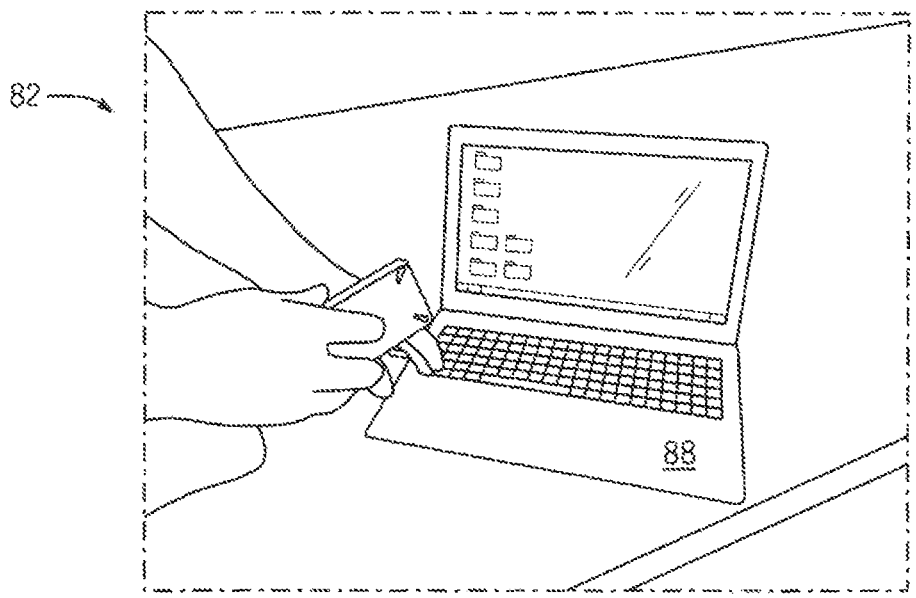

FIG. 9 illustrates using a system and method to enable persons or groups of persons to login and access computer and network resources and devices such as PCs, workstations, laptops, mobile devices and the like. The system 80 comprises an IMDT 82, a reader 84, a controller 86, a power supply 87, and a PC, workstation, laptop, mobile device, or any other electronic device 88. FIGS. 15A and 15B show an embodiment of a method of logging on to a laptop 88 via the method including the steps of reading a user's implanted chip 20/82 at a login screen and verifying a successful login to the operating system home screen of the laptop 88.

Figure 10:
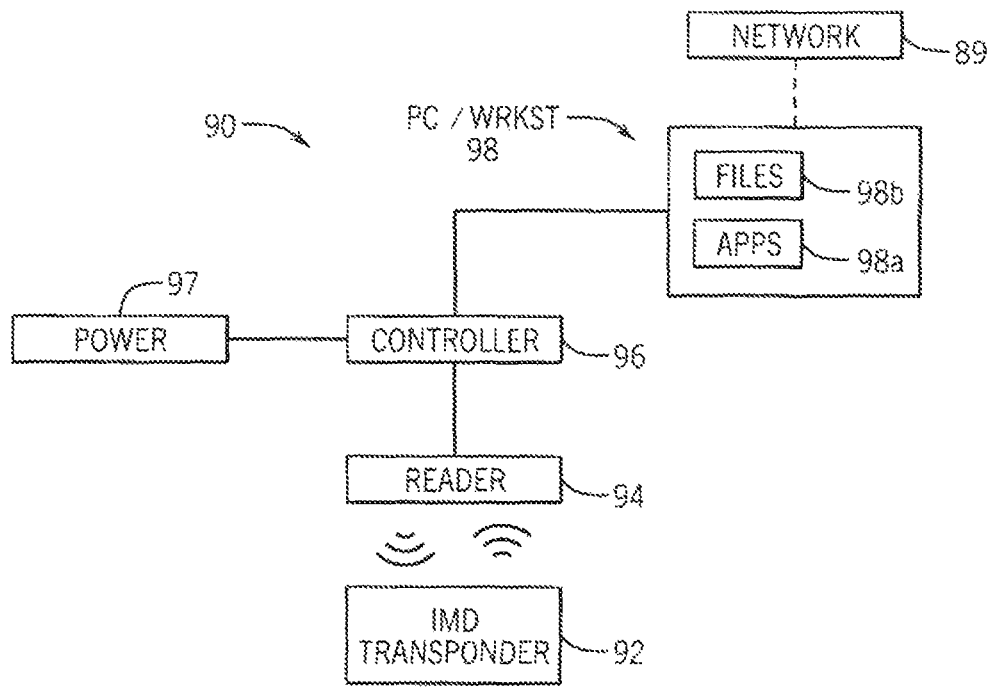
FIG. 10 illustrates an embodiment of the system and method to enable persons or groups of persons to login and access files, applications, apps and data resident on a particular computer and network resources and devices.

FIG. 10 illustrates using a system and method to enable persons or groups of persons to login and access files, applications, apps and data resident on a particular computer and network resources and devices. The system 90 comprises an IMDT 92, a reader 94, a controller 96, a power supply 97, and a PC, workstation, laptop, mobile device, or any other electronic device 98 that includes various apps 98a, files 98b or other applications or data. The device 98 may further be connected to a wired, wireless or wide area network 99.

Figure 11:
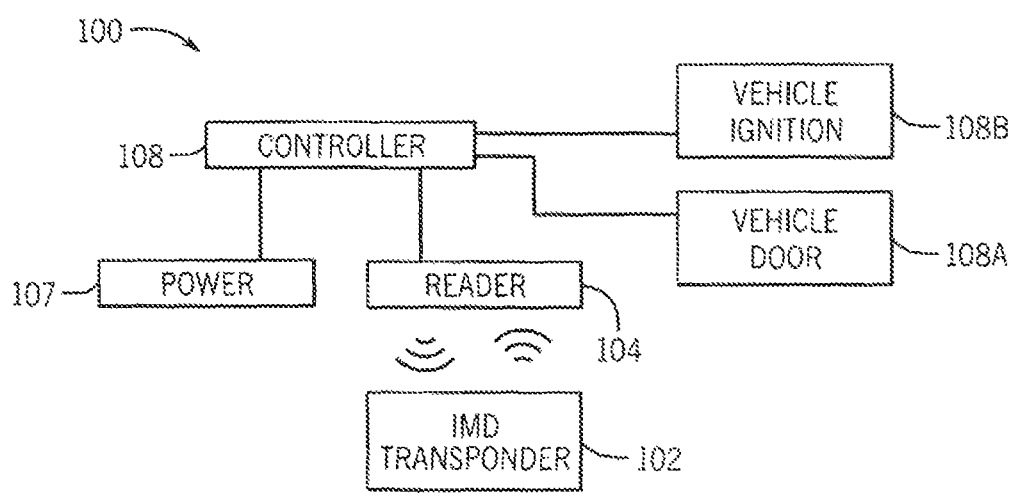

FIG. 11 illustrates using a system and method to enable persons or groups of persons to access and start a vehicle, such as an automobile, truck, bus, and the like. The system 100 comprises an IMDT 102, a reader 104, a controller 106, a power supply 107, and a door 108a and/or ignition 108b of a vehicle 108 such as an automobile, truck, bus, aircraft, watercraft or the like.

Figure 12:
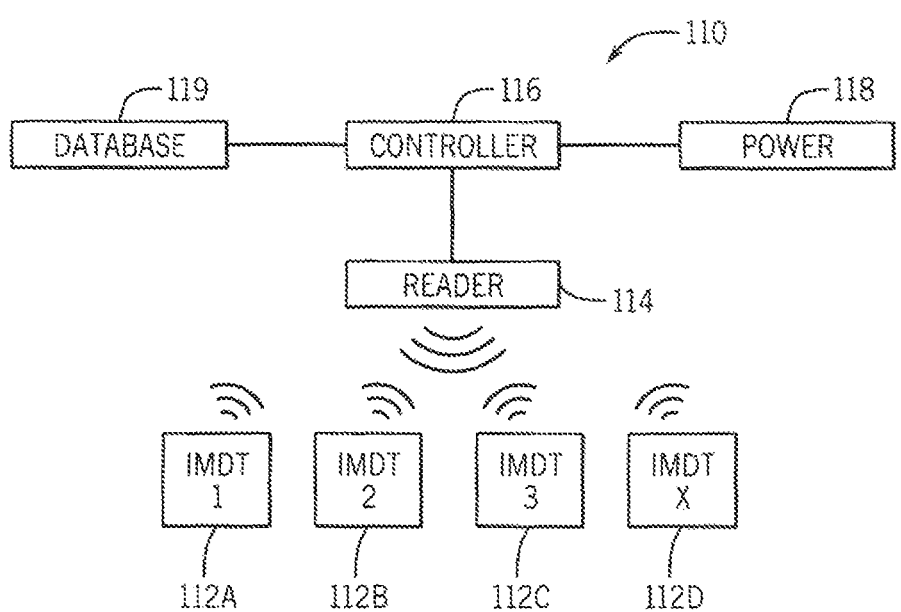
FIG. 12 illustrates an embodiment of the system and method of the in to enable a group of persons, such as employees or members of a group to perform certain tasks.

FIG. 12 illustrates an embodiment of the system and method of the invention to enable a group of persons, such as employees or members of a group to perform certain tasks. The system 110 includes an implantable micro device (IMD) transponder 112a to x (IMDT), each individually implanted in a user/member of the group. The system 110 further includes a reader 114 adapted to send signals, for example RF signals, to the chip 112, and to receive information from the chip 112. The reader 114 is communicatively connected to a controller 116. The controller 116 is connected to power 118. The controller 116 is also communicatively connected to a database 119, either internally or externally located. The controller 116 may be further connected to a variety of other devices or elements, such as a door lock or other mechanical device, a display, an input device(s), various communication devices or links, and the like.

Figure 16:
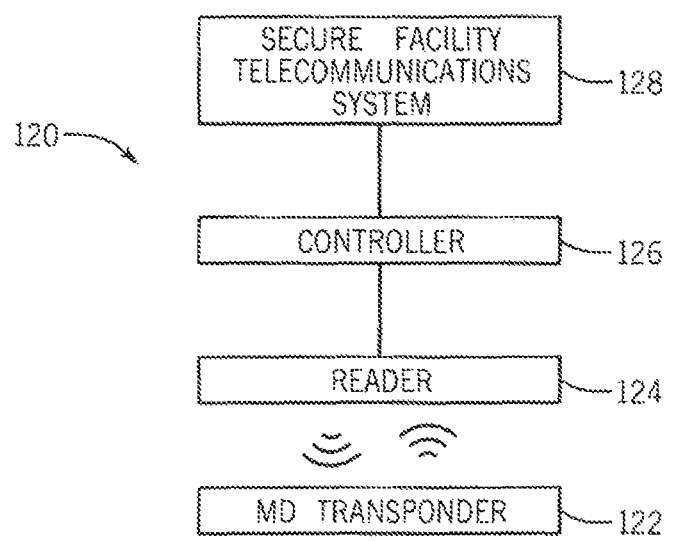
FIG. 16 illustrates an embodiment of the system and method of the invention to enable a group of persons, such as inmates of a secure facility, to access and use telecommunications resources (for example telephones or video kiosks) to make and receive calls or video visitations.

FIG. 16 illustrates an embodiment of the system and method of the invention to enable a group of persons, such as inmates of a secure facility, to access and use telecommunications resources (for example telephones or video kiosks). In particular, the system and method permit residents of the secure facility to receive incoming voice calls or video visitations. The system 120 includes a micro device (MD) transponder 122a to x (MDT), each individually coupled to a resident of a secure facility, for example by a strap disposed on the wrist or ankle of the resident. The system 120 further includes a reader 124 adapted to send signals, for example RF signals, to the chin 122, and to receive information from the chip 122. The reader 124 is communicatively connected to a controller 126. The controller 116 is communicatively connected to the telecommunications system 128 of the secure facility. An embodiment of the telecom portion 128 of the system 120 is disclosed in U.S. Pat. No. 9,578,162, issued Feb. 21, 2017, entitled Telecommunications Technology, which is owned by applicants' assignee. U.S. Pat. No. 9,578,162 is hereby incorporated by reference.

Figure 17:
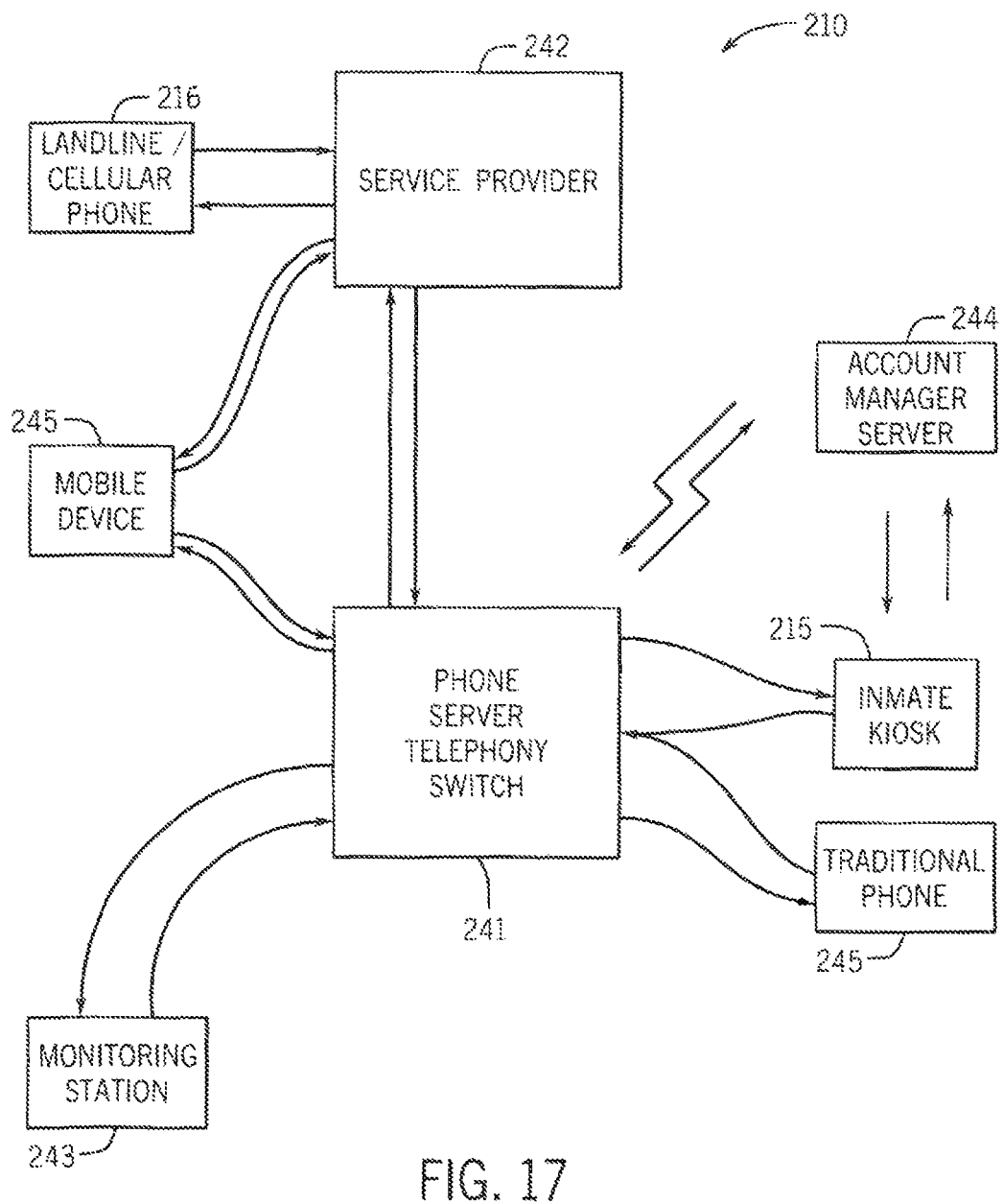
FIG. 17 is a more detailed diagram of the system of the invention, including the interconnection of a phone server and an account manager server, and a monitoring station of the system.

The telecommunications system 128 is shown in FIGS. 17-20 as system 210. Referring to FIG. 17, the system 210 comprises a phone Server 241, a telephony switch which is connected to a Service Provider 242. The Service Provider 242 is any provider with Session Initiated Protocol (SIP) capability. The Phone Server 241 negotiates SIP communication between various SIP endpoints. It handles call permissions as well as charging, recording and monitoring. The Phone Server 241 is communicatively connected to a Monitoring Station 243 which requests recorded and live streams from the Phone Server 241. Based on a request, the monitoring station 243 has the ability to pause, fast forward and rewind the recorded stream as well as to stop a live call in progress. It also enables calling rules. The Phone Server 241 is also communicatively connected to an Account Manager Server 244. The account manager 244 provides a means for the telephones to know the details of the caller and the person or entity being called. A most preferred example of the account manager server 244 is a Team Server provided by Team Software of Hudson, Wis. USA. However. The account manager server 244 can be any server that handles TCP/IP protocols over any IP network. The Phone Server 241 and Account Manager Server 244 are communicatively connected to the Inmate Kiosk(s) 215 or other devices inside the jail or other facility. Such other devices include traditional inmate telephones 219a and mobile or hand field devices inside the secure facility or jail. The Phone Server 241 is also communicatively connected to the telephones and devices 216a-c outside the facility.

Figure 18:
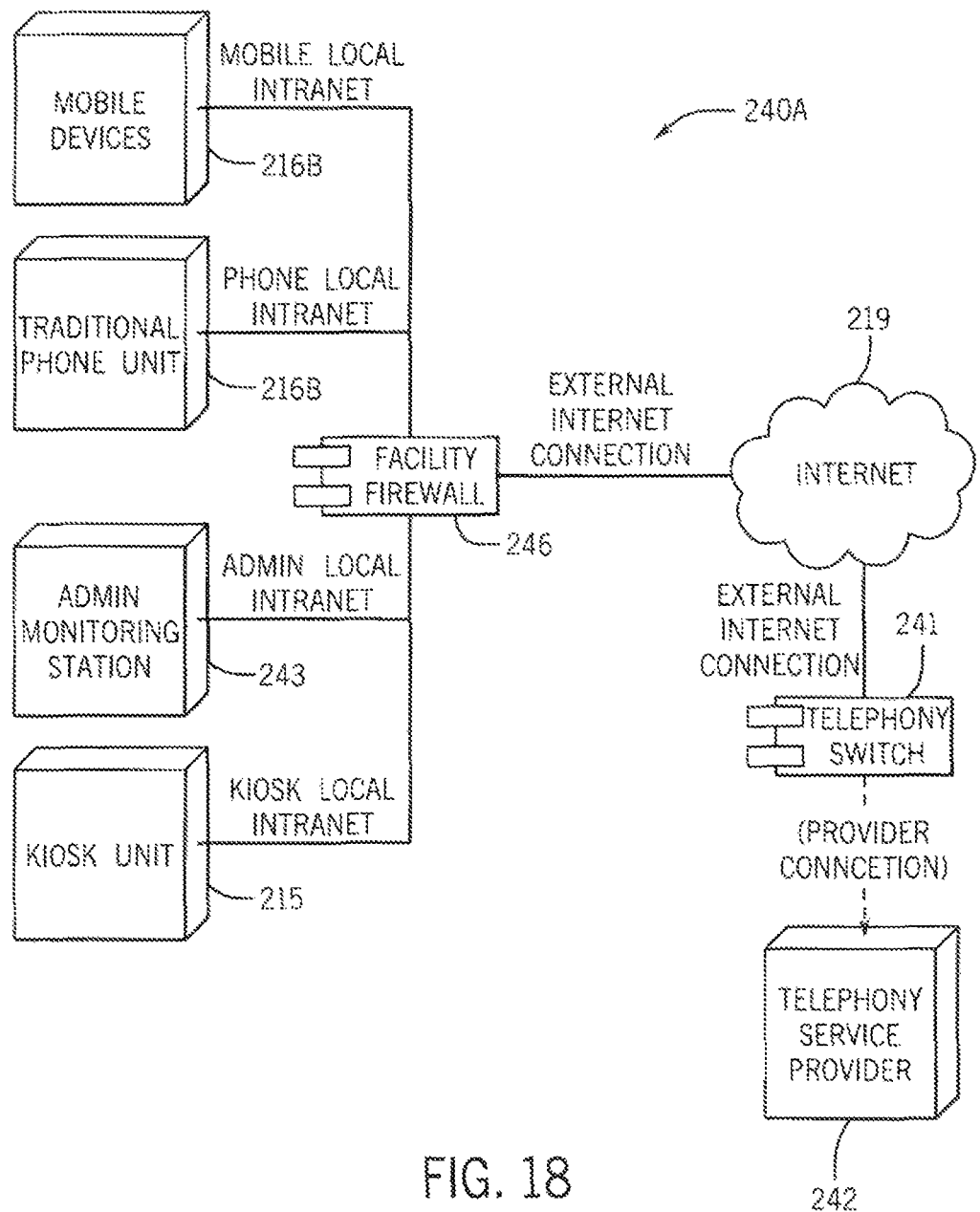
FIG. 18 a diagram showing an embodiment of the communicative interconnection of the phone server with elements of the system which are disposed inside the secure facility.

FIG. 18 shows an embodiment of the communications connections 240a between the phone server 241 and certain elements of the system 210 located inside the secure facility (the kiosk(s) 215, traditional inmate phone(s) 245, other mobile devices 216 in the facility, and the admin monitoring station 244) via the Internet 219 and through the facility firewall 246.

Figure 19:
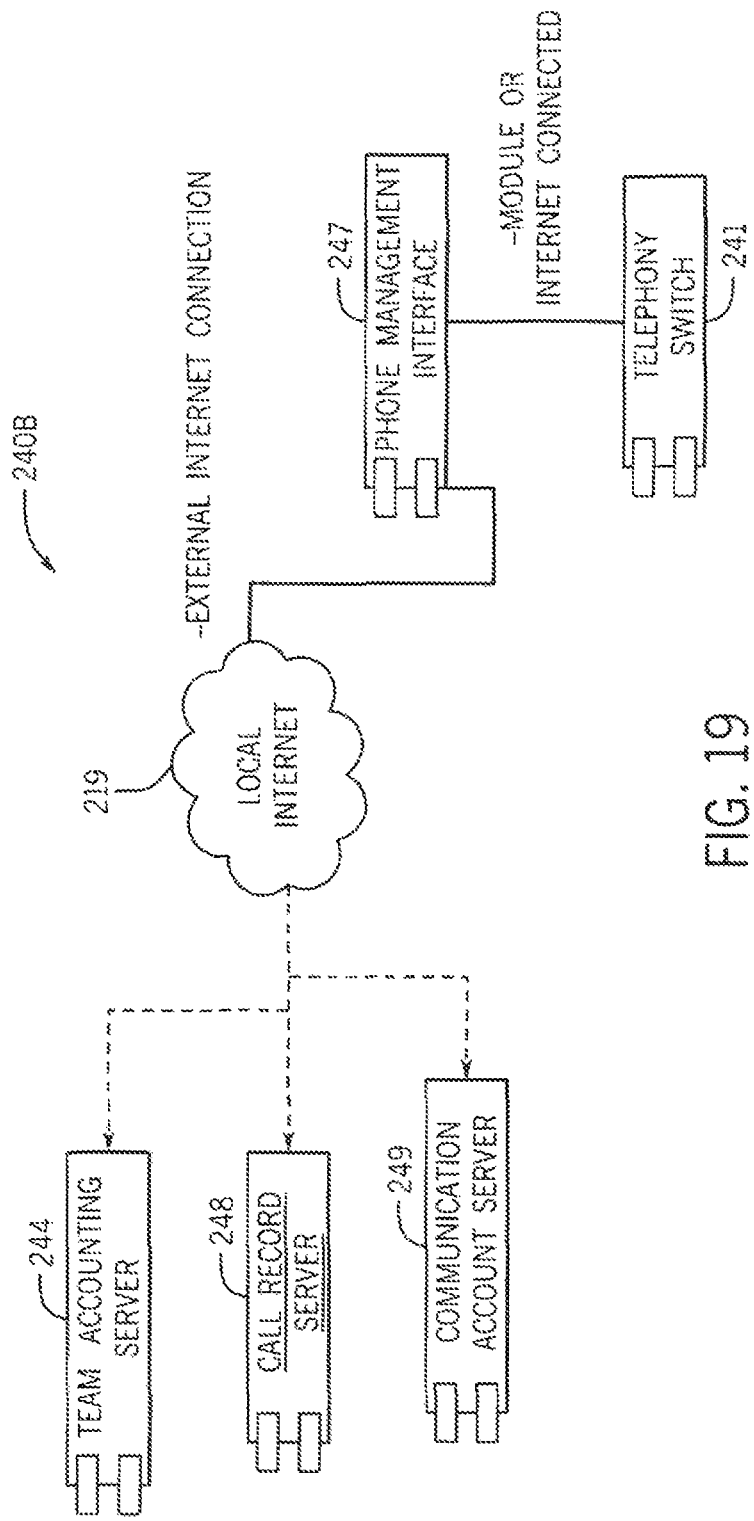
FIG. 19 is a diagram showing an embodiment of the communicative interconnections of the phone server with elements of the system which are preferably disposed outside the secure facility.

FIG. 19 shows an embodiment of the communication connections 240b between the phone server 241 and other servers and elements of the system 210 which are disposed outside the secure facility. The phone server 241 is preferably a software element which makes the calls. A phone management interface 247 is an additional layer of software that controls the phone server 241. The phone management interlace 247 processes information such as outgoing and incoming rules, the inmate rate, and the like. Connected through the Internet 219 are the account manager server 244, the call record server 248 (a hardware element which actually stores recorded calls), and a communication account server 249. The communication account server 249 is preferably software which debits and credits accounts at the manager of the system 210, and other similar business functions. The manager of the system 210 is preferably an independent third party business, such as Applicant's assignee. However, it is within the purview of the invention that the system 210 manager may be the jail or secure facility itself, or some other governmental, quasi-governmental or non-profit entity.

Figure 20A:
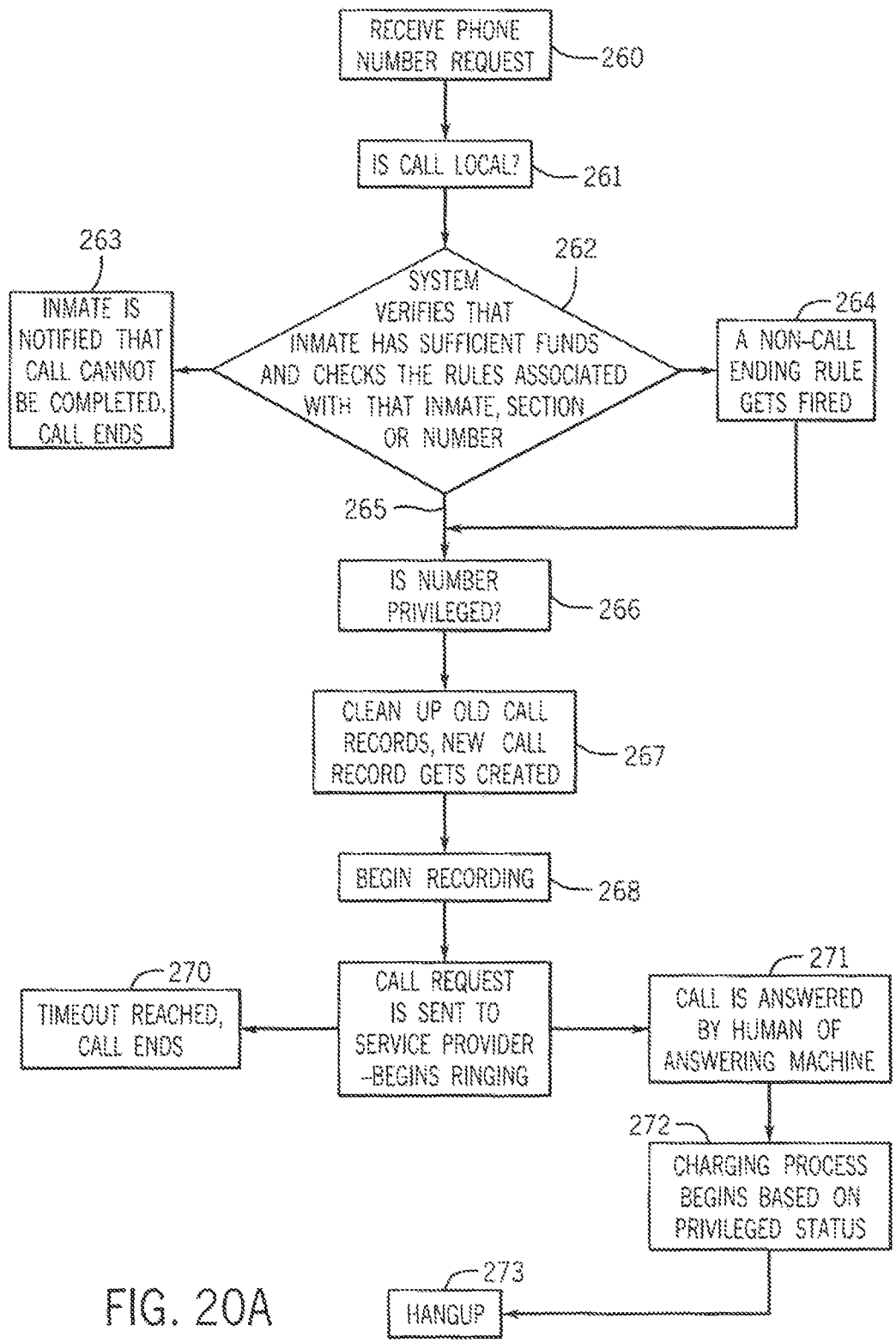
FIGS. 20a and 20b are flowcharts of an embodiment of an outgoing and an incoming call process, respectively, of the invention.

FIG. 20a is a flow chart showing an embodiment of the process of making an outgoing call from a jail according to the invention. The outgoing call process of the invention is preferably implemented by the system 210 of the invention. The first step of the process involves receiving 260 a request for an outside phone number of a family member, friend or other call recipient, and then determine 261 whether the call is local or long distance. Next, the system verifies 262 that the inmate has sufficient funds or credit, and checks associated rules for that inmate account. The call is either prohibited 263 (with notice to the inmate), a non-call ending rule is noted 264, or the system proceeds 265 to determination 266 whether the call number is privileged as for example in the case of an attorney telephone number. Proceeding with the call, next records are logged and created 267, recording is initiated 268 and the call is sent 269 to the service provider to ring the call recipient. If a timeout timer period is reached 270 the call ends. If the call is answered 271 within the allotted time, the call proceeds. A charging process 272 begins in some cases. The call proceeds until termination or hang up 273.

Figure 20B:
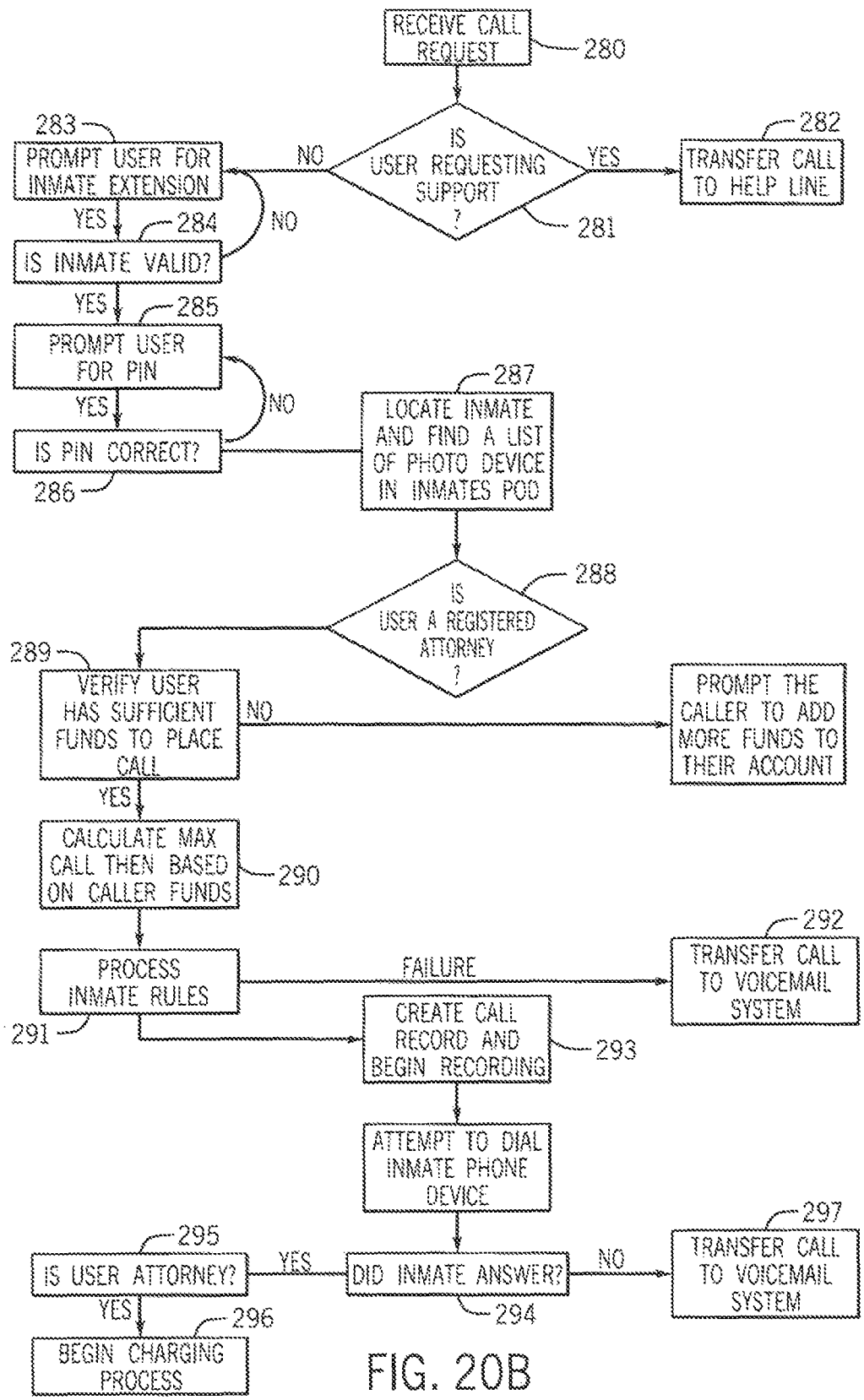

Significantly, the system of the invention provides a means of receiving 280 an incoming call to the inmate in the facility from a person outside. Referring to FIG. 20b, a preferred embodiment of an incoming call process of the invention involves first receiving a call request and then determining 281 whether the outside caller is requesting support. If so, then the call is transferred 282 to a help line. If not, the user is prompted 283 to dial or otherwise input an extension for the inmate. Users may first obtain an inmate extension as well as a PIN number by utilizing the inmate-cantee.com process. Next, the system determines 284 if the extension is valid. If not, then the caller has an opportunity to enter another extension by another prompt 285. If valid, the system inquires of the PIN and checks 286 whether it is valid. If the PIN is not entered correctly, the user again has an opportunity to correct. If the PIN is correct, the next step 287 is to find the Inmate's location and a list of phone devices in the inmate's POD (jail location). Phone devices main include, but are not limited to stand alone Kiosks, traditional hand held telephone devices and the like. The system then determines 288 whether the caller is a registered attorney. If the user is a registered attorney (again, preferably signed up at the inmatecanteen.com system), the conversation is private and a reduced rate may apply. If not, the system verifies 289 that the user has sufficient funds to place the call (funds are deposited via inmatecanteen.com). Maximum call time is calculated 290 based on caller funds, and at a predetermined time, for example the 1 minute 30 second remaining mark of the call, a blocking prompt is played warning the user that they are about to run out of call minutes. Initially or at any time later, inmate rules 291 may be processed. Such rules may include, but are not limited to inmate blacklisting, section/pod blacklisting, email call notifications, and approved calling hours. If a call or call event or time fails a rule, the call is transferred 292 to a voicemail system. If all rules or some rules are met, a call record is created 293, recording begins (unless attorney or other call), and the registered device is dialed. Recordings are processed in GSM format. Both sides of the stream are included in the recording. The next step is to wait 294 for an answer. If the inmate answers, the attorney rule is chocked 295 and if positive, the charging 296 process begins. If the inmate dots not answer, the call may be transferred 297 to a voicemail system.

Figure 21:
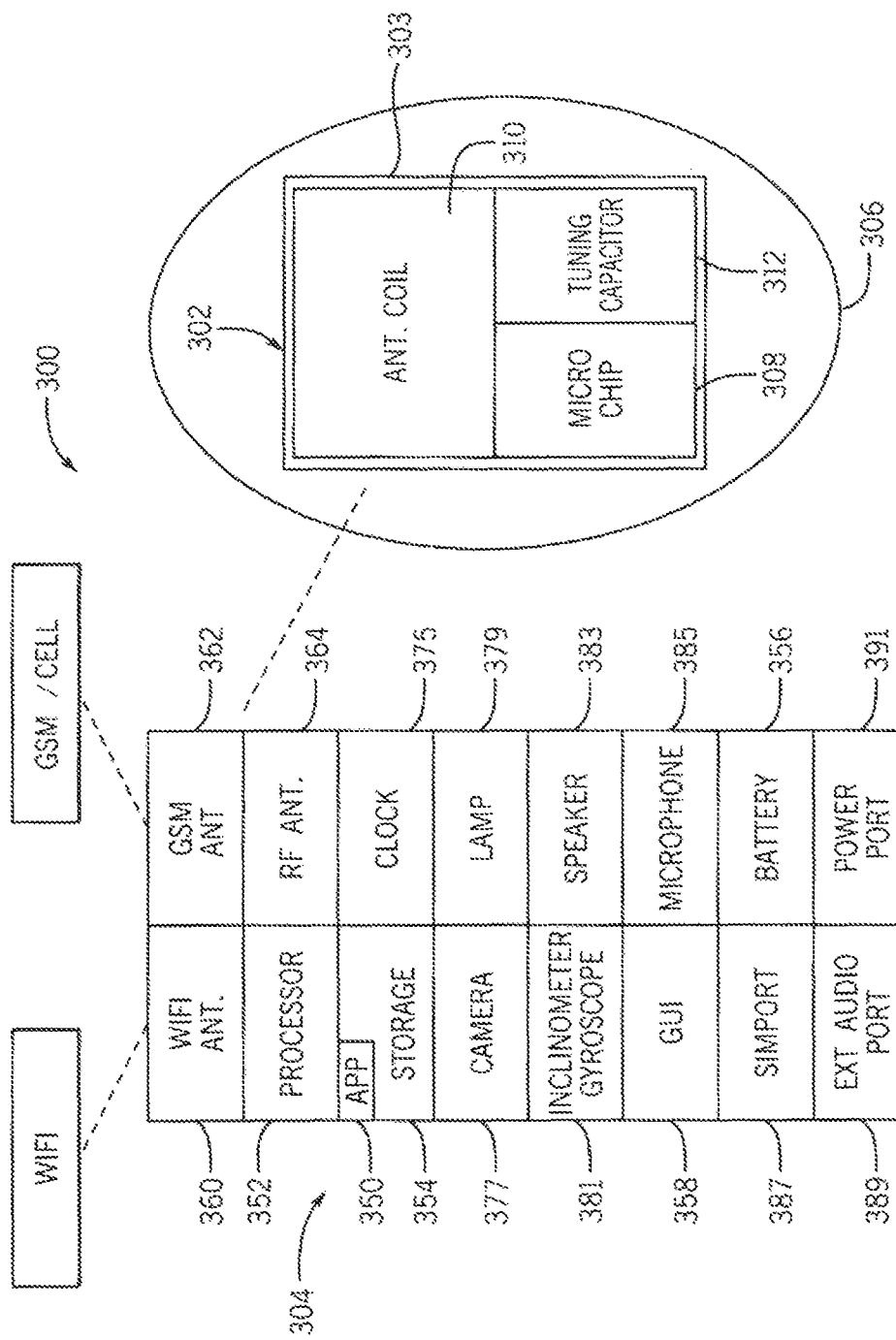

FIG. 21 shows an embodiment of the system 300 of the invention comprising an implantable or wearable micro device 302 and a mobile device 304. The micro device 302 is implanted in a body 306 of an animal such as a human being. Alternatively, the device 302 may be carried or worn by a person by way of a strap, pin, necklace, bracelet, anklet, belt or the like. The micro device has a microchip or integrated circuit 308 that may have one or more of the following sub components: micro-processor, programmable logic controller (PLC), data storage, transmitter/receiver, and the like. The device 302 further has a housing 303, an RF antenna coil 310 preferably tor sending and receiving signals, and a tuning capacitor 312. The micro device 302 is of course very small. At least because of its small size, it's features are inherently limited.

The mobile device 304 is preferably a smart phone, pod device or tablet device, laptop, notebook or other portable device having a processor, storage and other features, and which includes a software app 350 for interfacing with the micro device 302. The mobile device may have an iOS (Apple™), Android (Google™) or other operating system. The mobile device 302 has a processor 352 (typically higher performance than that of the micro device 302), data storage 354 (in which the app 350 is stored), a battery 356, a graphical user interface 358 (GUI), and means to transmit and receive signals. The means to transmit includes one or more of a Wi-Fi or other Wireless Local Area Network (WLAN) antenna 360, a GSM or other cellular network antenna 362, and an RF antenna 364. These antennae may be connected directly to the processor 352, or via a send/receive interface (not shown). The app 350 permits communication to, from, or preferably to and from the mobile device 304 and the micro device 302. This permits setup and/or control of the micro device 302. It also permits transfer of information front the micro device 302 to the mobile device 304. From there, the information may be communicated remotely via Wi-Fi or cellular communication. The system also permits processing and/or simple storage of information acquired by the micro device 302 by the mobile device 304.

Significantly, the mobile device 304 may have other features that may be harnessed by or shared with die micro device 302. These features may include one or more of the following devices: a clock 375, a camera 377, a lamp 379, an inclinometer and/or gyroscope 381, a speaker 383, and/or a microphone 385. The mobile device 304 may also have connectors for external devices and systems, such as a SIM port 387 or other means to store mobile subscriber identity, an external audio port 389, and a power charge port 391. The ability to interface with the clock 357 permits the micro device 302 to perform clock and timing functions such as synchronizing with respect to time, alarm and other functions. The camera 377 and lamp 379 interconnection permits photo or video functionality. The inclinometer gyroscope 381 and/or the standard location services of the mobile device 304 permit tracking and other location services for the chip 302. The speaker/microphone 383/385 permit audio recording and play, alarm and other audio functionality. The external ports 387, 389 and 391 permit interfacing of the chip 302 with a variety of external devices.

Figure 22:
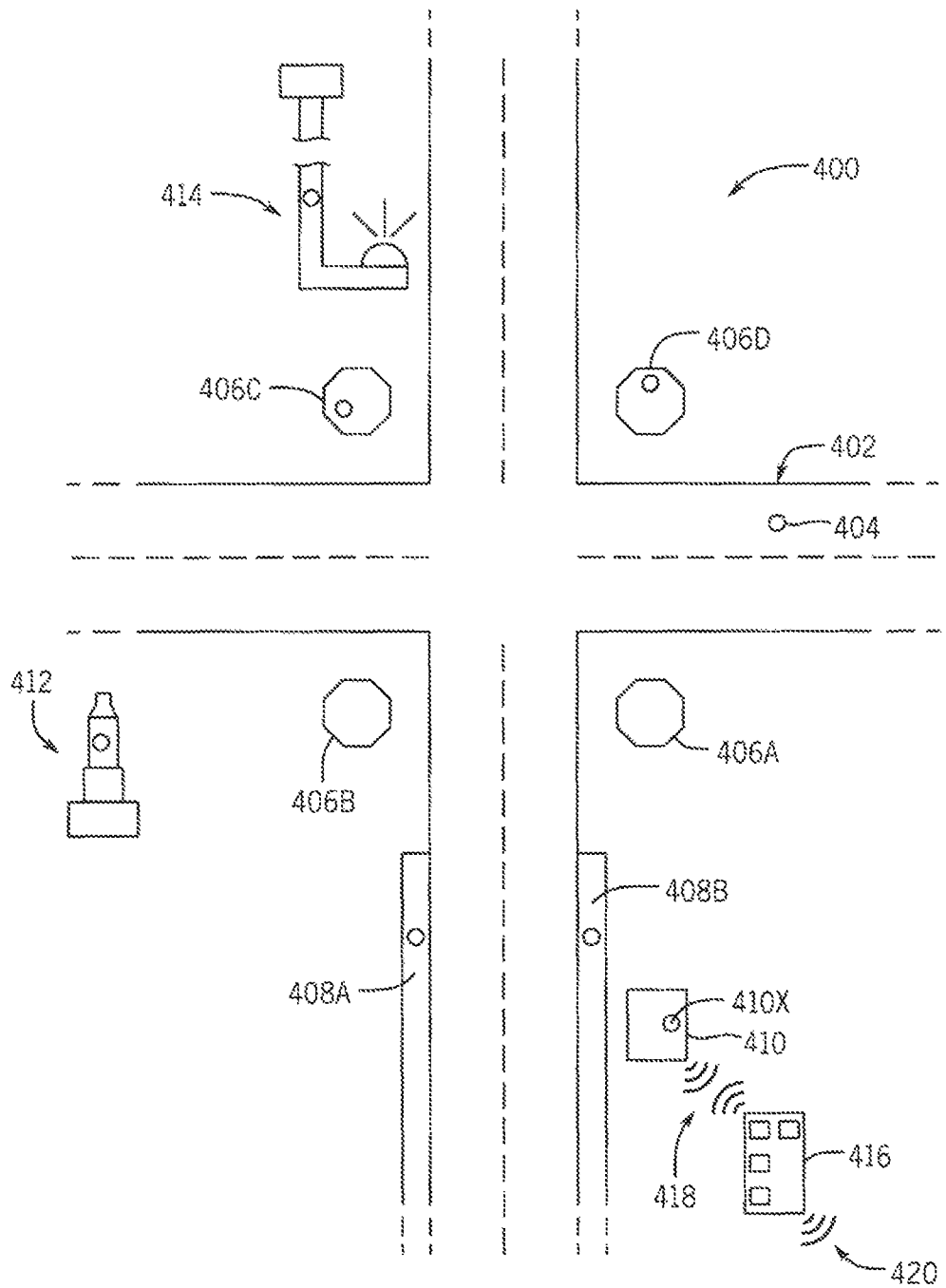
FIG. 22 shows an embodiment of yet another alternative system of the invention which includes micro devices embedded in, incorporated into, or otherwise attached to articles, devices, structures or things for geo-location or other services such as tracking, monitoring, or management.

FIG. 22 shows an embodiment of yet another alternative system of the invention which includes micro devices embedded in, incorporated into, or otherwise attached to articles, devices, structures or things for geo-location or other services such as tracking, monitoring, or management. In the embodiment, a municipality 400 has a series of streets or roads 402 with related resources. Examples of these include a plurality of stop signs 406*a-b*, speed limit or other information signs 408, fire hydrants 412, lights 414 and the like. The roadway 402 may have features such as curbs 408. Although the features shown are primarily fixed in place, they or other resources may be movable. A need exists for the municipality to manage them by inventory (age, condition and the like), tracking their location, mapping, and to manage them for maintenance, replacement and the like. The system of the invention provides micro devices that are embedded in the resource, attached to them by tags, labels, fasteners, adhesives, welds or the like, or incorporated into the resources during manufacture. For example, micro device 402 is embedded into the roadway 404 at a predetermined location to monitor location, temperature, pressure, humidity, age, wear and other parameters. Another example is device 410*x* affixed to traffic information sign 410.

In use, a mobile device 416 (such as a smart phone with an app or a dedicated hardware scanner) is brought into proximity with the tag 410*x* and communicates with it via an RF or other short range signal 418. Features on the device 416 permit processing of information on site, or transmission of information via long range signals 420 such as Wi-Fi or cellular transmission.

In addition to the systems and methods being used for commissary purchasing and telecommunications resource use in secure facilities such as detention centers, jails and prisons, described above, these systems and methods may further be used to monitor the location and movement of facility residents by having a resident check-in or otherwise indicate their presence at or to a predetermined location, including at a predetermined time(s). So, for example, the system and method could be used as a bed check means, to indicate that the resident is at their assigned quarters or cell at or near the end of the day. It could also be used to verify the presence of the resident at a job or other assigned task site, meal time, or other predetermined lime or event.

The embodiments above are chosen, described and illustrated so that persons skilled in the art will be able to understand the invention and the manner and process of making and using it. The descriptions and the accompanying drawings should be interpreted in the illustrative and not the exhaustive or limited sense. The invention is not intended to be limited to the exact forms disclosed. While the application attempts to disclose all of the embodiments of the invention that are reasonably foreseeable, there may be unforeseeable insubstantial modifications that remain as equivalents. It should be understood by persons skilled in the art that there may be other embodiments than those disclosed which fall within the scope of the invention as defined by the claims. Where a claim, if any, is expressed as a means or step for performing a specified function it is intended that such claim be construed to cover the corresponding structure, material, or acts described in the specification and equivalents thereof, including both structural equivalents and equivalent structures, material-based equivalents and equivalent materials, and act-based equivalents and equivalent acts.

The invention claimed is:

1. A method of interrogating a microdevice for information, comprising steps:
   A. providing a Radio Frequency (RF) microdevice having (i) a housing, (ii) an antenna disposed inside the housing, (iii) a microprocessor disposed inside the housing and communicatively connected to the antenna, (iv) a tuning capacitor disposed inside the housing and communicatively connected to the microprocessor, and (v) at least one transducer, and wherein an electronic identification code is stored in or by the microprocessor;
   B. attaching, subcutaneously, the RF microdevice to a person, wherein the microdevice is a Radio Frequency Identification (RFID) chip;
   C. providing an RF login system, the RF login system including:
      i. at least one RF reader disposed at a predetermined location on or near the RF microdevice, and
      ii. at least one login processor communicatively connected to the at least one RF reader and to the microprocessor of the RF microdevice, the at least one login processor having means to corroborate the electronic identification code on the RF microdevice;
   D. the person brings the RF microdevice near the at least one RF reader, whereby:
      i. the at least one RF reader communicates with the RF microdevice via RF signals, and
      ii. the at least one RF reader signals the at least one login processor to corroborate the electronic identification code, and
         (1) if the at least one login processor corroborates the electronic identification code, the at least one login processor signals the RF microdevice microprocessor to permit access to information from the at least one transducer, or
         (2) if the at least one login processor does not corroborate the electronic identification code, the at least one login processor signals the RF microdevice microprocessor to not permit access to the information from the at least one transducer.

2. The method of claim 1, wherein the at least one transducer is selected from a group consisting of a location transponder, a thermometer, a heart rate transducer, a blood pressure transducer, and an information storage memory element.

* * * * *